US005515870A

United States Patent [19]
Zilber

[11] Patent Number: 5,515,870
[45] Date of Patent: May 14, 1996

[54] THUMB AND FINGER SUCKING PREVENTION DEVICE

[76] Inventor: Eugene A. Zilber, 815 Tadlock Pl., Matthews, N.C. 28105

[21] Appl. No.: 709,804

[22] Filed: May 31, 1991

Related U.S. Application Data

[63] Continuation of Ser. No. 512,330, Apr. 23, 1990, abandoned.

[51] Int. Cl.⁶ ......................................................... A61F 5/37
[52] U.S. Cl. ................................................ 128/878; 128/880
[58] Field of Search ................................... 128/878–890; 2/338, DIG. 7, 75, 80, 311; 24/314, 662, 324

[56] References Cited

U.S. PATENT DOCUMENTS

| | | |
|---|---|---|
| 90,678 | 9/1833 | Parke . |
| 490,733 | 1/1893 | Armat ........................ 128/880 |
| 1,048,569 | 12/1912 | Mitchell .................... 128/880 |
| 1,161,478 | 11/1915 | Jackson ..................... 128/880 |
| 1,345,783 | 7/1920 | Kelly ........................ 128/880 |
| 1,561,631 | 11/1925 | Winter ....................... 128/880 |
| 1,584,999 | 5/1926 | Thompson ................... 128/880 |
| 1,633,037 | 6/1927 | Rood ........................ 128/880 |
| 1,652,867 | 12/1927 | MacLachlan ................ 128/880 |
| 1,733,933 | 10/1929 | Beltz ........................ 128/880 |
| 1,990,384 | 2/1935 | Klohs ....................... 128/880 |
| 2,074,113 | 3/1937 | Hovey ....................... 128/880 |
| 2,127,421 | 8/1938 | Paul ......................... 128/880 |
| 2,536,633 | 1/1951 | Fitch ........................ 128/880 |
| 2,633,126 | 3/1953 | Newmark .................... 128/880 |
| 2,684,065 | 7/1954 | Umbenhower ............... 128/880 |
| 2,688,961 | 9/1954 | Thomas ..................... 128/133 |
| 2,798,482 | 7/1957 | Feeney ...................... 128/133 |
| 3,442,267 | 5/1969 | Krygier ..................... 128/133 |
| 4,396,014 | 8/1983 | Pace ......................... 128/880 |
| 4,665,907 | 5/1987 | Leverette ................... 128/880 |

Primary Examiner—Michael A. Brown
Attorney, Agent, or Firm—Philip J. Pollick

[57] ABSTRACT

This invention is a device for the prevention of thumb and finger sucking that utilizes a vacuum-breaking device such as a cylinder that is placed over one or more fingers or the thumb and prevents the formation of a sucking vacuum by utilizing air passages in or between the vacuum-breaking cylinder and the thumb or fingers. The vacuum-breaking cylinder is secured to the hand by means of a wrist band and a suitable means, such as one or more straps, for connecting the vacuum-breaking cylinder to the wrist band.

16 Claims, 2 Drawing Sheets

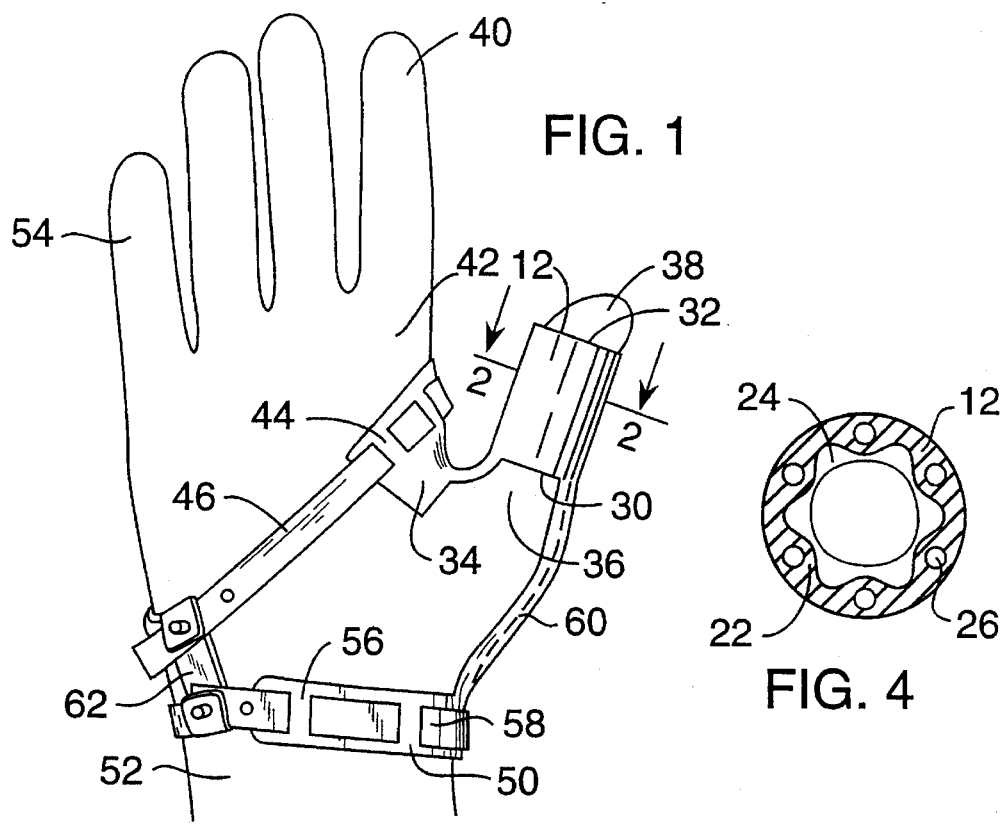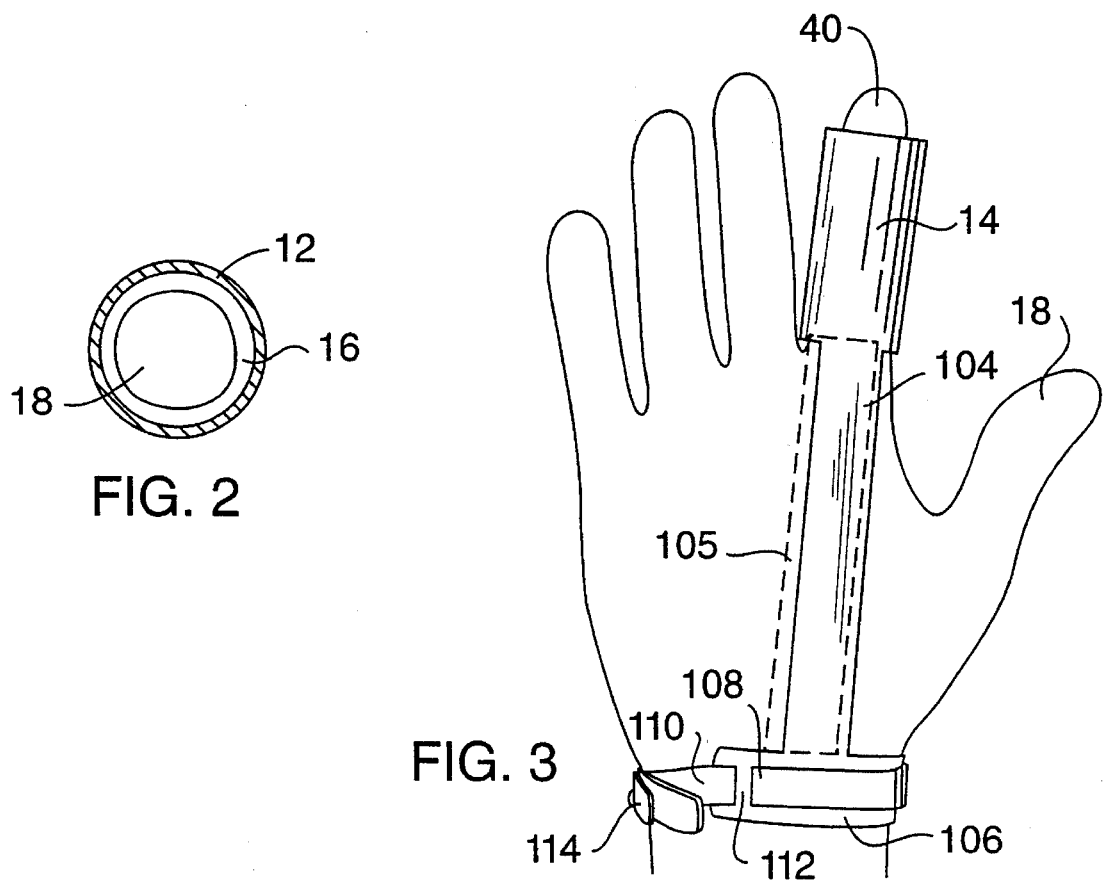

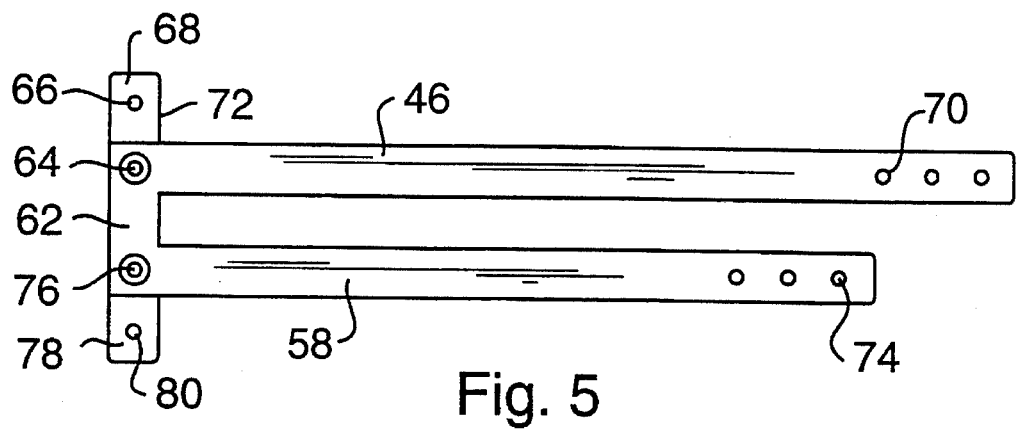
Fig. 5
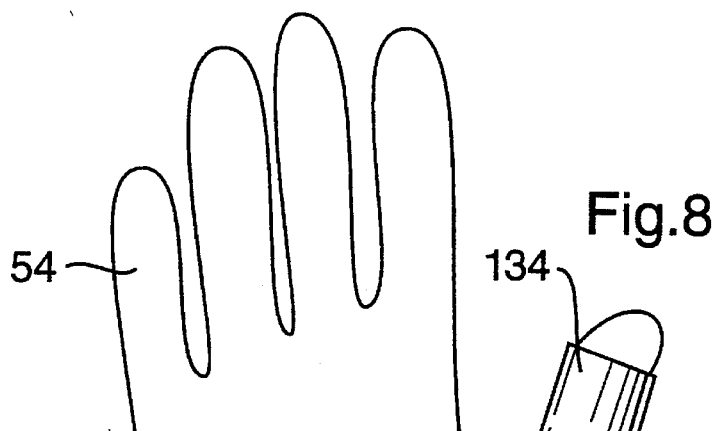
Fig. 8
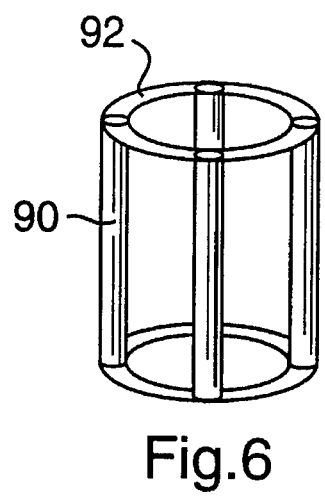
Fig. 6
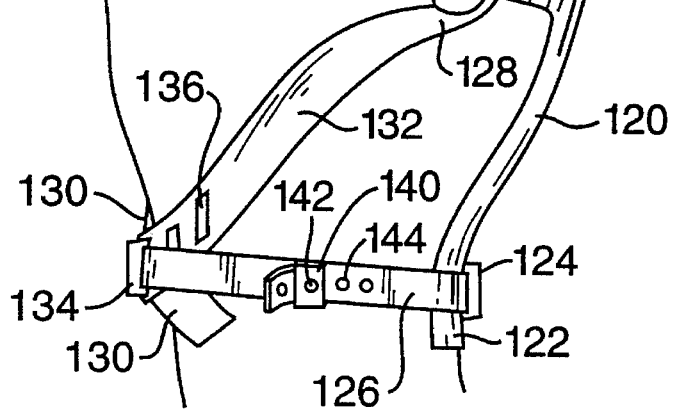
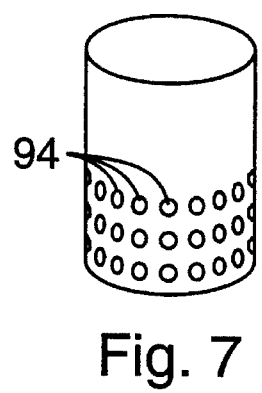
Fig. 7
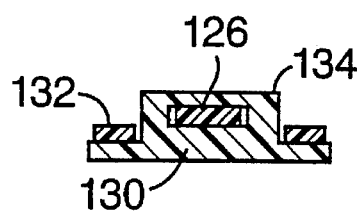
Fig. 9

THUMB AND FINGER SUCKING PREVENTION DEVICE

This is a continuation of our prior application Ser. No. 07/512,330; filed Apr. 23, 1990, now abandoned.

FIELD OF THE INVENTION

This invention relates to a device for the prevention of thumb and finger sucking. More particularly, it relates to a vacuum-breaking device for the prevention and discouragement of thumb and finger sucking.

BACKGROUND OF THE INVENTION

Generally, thumb sucking has been treated in three general ways in the past. In the first method, the thumb is coated with a substance which creates an unpleasant taste in the child's mouth. For example, the thumb is coated with an unpleasant tasting substance such as lemon juice or similar substance. In the second method, the thumb and fingers are completely covered or restrained so that the child is not able to insert them into its mouth. For example, the sleeves of the garment which the child is wearing may be pinned or otherwise closed or a glove or similar type device may be placed over the child's hand. In the third method, an object is substituted for the thumb or finger. Such devices include devices such as teething rings or pacifiers.

U.S. Pat. No. 2,688,961 to Thomas (Sep. 14, 1954) shows a teething ring that may be attached to the finger or thumb. U.S. Pat. No. 2,798,482 to Feeney, discloses a hand-attached device such as a pacifier or teething device. U.S. Pat. No. 3,442,267 to Krygier shows a hand covering mitt which includes proturbances which are capable of acting as pacifiers. Design patent 90,678 to Parke shows an ornamental design for an anti-thumb sucking device.

All of the prior art devices have disadvantages including: 1) the restraint of the child when using the glove type or sleeve restraint, 2) unpleasant tastes for the child using various chemical compositions that are applied to the fingers and thumb, 3) the substitution of one device, i.e., the pacifier for the thumb or finger which substitutes one form of behavior for another but does not eliminate the objectionable sucking habit, and 4) in the case of sufficiently small device, the creation of a potential for choking on the device.

SUMMARY OF THE INVENTION

The present invention solved these problems with a device that discourages or prevents thumb sucking to break the thumb-sucking habit without the use of a substitute pacifier, untasteful chemical compositions, or the restraint of the child's hand or fingers. The device can be worn by a child without discomfort or restraint of normal activity. In its simplest form, the device consists of a vacuum-breaking device, such as a cylinder, that is placed over at least one digit of the hand where the term "digit" includes the four fingers and the thumb. The vacuum-breaking device is any object that generally conforms to the shape of the thumb or finger or portion thereof and allows for the free passage of air to the mouth of the child and thus prevents the formation of a sucking vacuum. In one embodiment of the invention, the vacuum-breaking device is a cylinder of a sufficient diameter so as to permit the passage of air from one end of the device to the other when it is placed over the finger or thumb of the child. Typically in such an embodiment, the vacuum-breaking cylinder has sufficient rigidity so that it does not collapse or otherwise form a vacuum seal between the cylinder and the thumb or finger.

Other embodiments may also be used to accomplish the vacuum-breaking function. For example, a cylinder device may have longitudinal ridges along the inner surface of the cylinder so as to form air passages in the valleys or channels between the ridges when the digit is in contact with the ridges. In another embodiment, air passages are formed into the device and are an integral part of the device. The air passages are positioned so that one end cannot be closed by the sucking action of the user. In another embodiment, a cylindrical device may have holes so located as to allow passage of air through the walls of the cylinder and then between the interior cylinder wall and the digit and into the user's mouth. In another version, the device may cover the end of the digit and have a wide base that allows air to be drawn into the interior of the device and then pass into the mouth of the user through holes in the device near the tip of the covered digit. In another embodiment one or more longitudinal tubes may be formed into a cylindrical shape using one or more annular bands to hold the tubes in a cylindrical shape that surrounds the digit. Such equivalent embodiments all illustrative only. Many other devices for performing the vacuum-breaking function when the thumb or finger is inserted into the mouth are possible and considered equivalent for this invention. Specific limitation in any embodiment are not meant as a limitation on the invention as a whole.

In order to prevent the device from being aspirated into the child's mouth where it may cause choking or possibly death, the vacuum-breaking device is secured to the hand of the child. For the purposes of this invention the term "hand" is defined as including the digits, the flat portion of the hand to which the digits are attached, and the wrist section of the lower arm to which the hand is attached. The device is typically attached to the hand by placing a band about the wrist that is sufficient tightness so as to prevent it from slipping over the flat portion of the hand. The vacuum-breaking device is attached to the wrist band. The means by which the vacuum-breaking device and the wrist bands are attached include cords, straps, or even a suitably designed glove with separate vacuum-breaking devices for some or all of the digits and a securing wrist portion, among others. The vacuum-breaking device, the wrist band, and the attaching means may be formed of one piece of material or they may be formed of individual pieces and suitably connected.

The wrist band may be secured about the wrist by using a locking button such as that used in hospitals for securing identification bracelets on a person's wrist. Typically such locking buttons are composed of a post and a hole of such dimensions that when the post is placed into the hole, the post and hole lock together and are unable to be taken apart. When using the locking button type mechanism to fasten the wrist band, it is anticipated that the locking portion of the device will be removed and thrown away daily or even at shorter intervals. A more permanent device can be made in which the wrist band is secured by buckle or other similar type securing mechanism.

In an embodiment of the invention for finger sucking, a hollow cylinder of sufficient size, i.e., diameter, is placed over one or more fingers of the user. The diameter of the hollow cylinder is of such size as to permit the flow of air from the base of the finger to the tip of the finger through the cylinder. A wrist band is placed around the wrist of the user and adjusted to a tightness so as to be incapable of being slipped over the hand of the user. Typically this band encircles the wrist and is joined at its ends by a fastening means such as a locking button or a buckle. In a simple embodiment of the device, the base of the vacuum-breaking cylinder is joined to the wrist band by means of a connecting part such as a strap that extends from the base of the vacuum-breaking cylinder to the wrist band. Typically, for a one strap joining means, the strap extends from the base of the vacuum-breaking cylinder to the wrist band over the back of the hand, that is, the band traverses the back of the hand from the base of the vacuum-breaking cylinder to the wrist band. In some instances, it is possible for a small child to bend its fingers backward for a sufficient distance to enable the vacuum-breaking cylinder to be pulled away from the finger. In such instances, it is desirable to use a second band that joins the cylinder to the wrist band on the opposite side of the hand, that is, if the first band traverses the back of the hand then the second band will traverse the palm of the hand.

A thumb sucking embodiment of the device may be made by forming a hollow vacuum-breaking cylinder that consists of a first and second end and has a diameter of sufficient size to enable the cylinder to fit over the thumb so that the first end is near the base of the thumb and the second end is near the end of the thumb. The vacuum-breaking cylinder forms an air passage between its interior wall and the thumb or otherwise contains one or more air passages that are capable of permitting the flow of air from the first end of the hollow cylinder to the second end of the cylinder. The thumb-sucking prevention device also consists of a wrist band of sufficient length to surround the wrist of the user with a means for fastening the first and second ends of the band with sufficient tightness around the wrist so that the band is incapable of being slipped over the hand of the user. For example, the hollow vacuum-breaking cylinder is attached to the wrist band in such a fashion so as to prevent the hollow-cylinder from being removed from the thumb. The hollow cylinder can be joined to the wrist band by means of a band that extends from the base of the hollow cylinder along the outside of the thumb to the wrist band. Two additional bands may be fastened to the base of the hollow cylinder near the inner base of the thumb. The first of these bands is joined to the wrist band in the area generally below the fifth digit of the hand and traversing the back of the hand in a diagonal fashion from the base of the thumb to the wrist area below the fifth digit of the hand. The second band passes over the front or palm of the hand and is also joined to the wrist band in the wrist area below the fifth digit of the hand. These two additional straps are joined to the wrist band by means of a suitable fastening device such as a lock button or buckle.

In another version of the previous device, the band that is joined to the base of the cylinder and extends along the outside of the thumb has one or more openings in the wrist area through which a wrist band can pass. These openings can be slits cut into the band through which the wrist band can pass or they can be either a soft or a rigid loop through which the wrist band can pass. A rigid loop enables the wrist band to be easily threaded therethrough.

The two additional bands that are joined to the cylinder near the inner base of the thumb are joined together in the wrist area below the fifth digit. A rigid loop in one band projects through an aperture in the second band. The wrist band is then threaded through the rigid loop. After passing through this loop and the loop on the band that extends along the outside of the thumb, the wrist band is secured to itself with appropriate means such as a lock button.

In another embodiment of the thumb-sucking version of the invention, the hollow vacuum-breaking cylinder is constructed as previously described with the following modifications. A webbed pad extends from the base (first-end) of the hollow cylinder on the inside of the thumb and conforms in shape generally with the webbed (muscle and skin) portion of the hand between the thumb and the index finger (second digit). The webbed pad has loops on it for cooperating with a securing strap which secures the webbed pad and attached hollow cylinder to the wrist band. A wrist pad conforms generally to the shape of the wrist with an open side in the wrist area generally below the fifth digit of the hand. The wrist pad has loops on it for cooperating with a securing wrist strap. These loops may be formed in various manners including the placement of vertical slits through the wrist pad to form loops.

A short vertical member is located in the open area of the wrist pad just below the fifth digit of the hand. This vertical member has a first and a second strap. The first strap traverses one side of the hand, is threaded to the loops on the webbed pad, and then traverses the opposite side of the hand and its end is fastened to the vertical member. The second strap of the vertical member encircles the wrist while simultaneously being threaded through the loops on the wrist pad. After encircling the wrist, the end of the strap is fastened to the vertical member. Preferably the straps are fastened to the vertical member with a suitable fastening device such as a lock button or buckle. Two separate fastening devices may be used for each strap or, alternatively, a single lock button may be used.

Other objects and features of the invention will be apparent and understood from the detailed description of the invention as the accompanying drawings which follow.

The foregoing and other advantages of the invention will become apparent from the following disclosure in which various embodiments of the invention are described in detail and illustrated in the accompanying drawings. It is contemplated that variations in procedures, structural features, and arrangement of parts may appear to the person skilled in the art without departing from the scope or sacrificing any of the advantages of the invention.

BRIEF DESCRIPTION OF THE DRAWINGS

FIG. 1 is either a front or a rear view of a thumb-sucking version of the present invention mounted on a user's hand;

FIG. 2 is a cross-sectional view of the vacuum-breaking cylinder of this invention taken on line 2—2 of FIG. 1;

FIG. 3 is a front or back view of a finger-sucking version of this invention mounted on the user's hand;

FIG. 4 is an alternate version of the vacuum-breaking cylinder of this invention taken on the line 2—2 of FIG. 1;

FIG. 5 is a plan view of the vertical member and straps that secure the thumb-sucking version of this invention to the user's hand.

FIG. 6 is a perspective view of an alternative embodiment of the vacuum-breaking cylinder.

FIG. 7 is a perspective view of a second alternative embodiment of the vacuum-breaking cylinder.

FIG. 8 is an alternate version of the invention shown in FIG. 1.

FIG. 9 is a cross section of the two tongues and wrist band of FIG. 8 at their point of intersection.

DETAILED DESCRIPTION OF THE INVENTION AND BEST MODE FOR CARRYING OUT THE PREFERRED EMBODIMENT

It is to be understood that FIGS. 1 and 3 may be considered as both a front and back drawing of the hand, that is, a view of the back of the hand or a view of the palm of the hand. It is further understood that representations shown in FIG. 1 and 3 are identical for both the front and back of the hand and that the embodiments shown in FIGS. 1 and 3 have essentially identical structure when viewed from the front and the back.

To further understand this invention it should be noted that the term "digits" refers to the four fingers and the thumb. The fifth digit is that digit which is furthest removed from the first digit, i.e., the thumb. The term "hand" is not limiting and can include the digits, the wrist section of the lower upper extremity, and the flat portion joining the digits and the wrist-the flat portion is often also referred to as the hand, or palm.

One of the key components of the invention is the vacuum-breaking cylinder 12 shown in FIG. 1 for the thumb 18 and a similar vacuum-breaking cylinder 14 shown in FIG. 3 for a finger 40. As shown in FIGS. 2 and 4, which are cross-sections of the vacuum-breaking cylinder 12 or 14, the vacuum-breaking cylinder permits the flow of air from one end to the other so as to break the sucking vacuum that a child experiences in sucking on either its fingers or thumb. As shown in FIG. 2, the vacuum-breaking cylinder may be simply a cylinder of a sufficient diameter as to enable the flow of air between the cylinder 12 and the finger 18 in passage 16. As shown in FIG. 4, the vacuum-breaking cylinder 12 may have ridges 22 that form air passageways 24 between the cylinder and the finger 18. The vacuum-breaking cylinder 12 may have vertical air passageways 26 that extend the length of the cylinder and that permit the flow of air therethrough. The passages 26, 24, and 16 are various ways in which a vacuum-breaking device may be achieved. These various means may be used either singularly or in combination. The vacuum-breaking device could simply be a series of vacuum-breaking tubes 90 permitting the passage of air therethrough and arranged around the finger and held together by one or more bands 92 as shown in FIG. 6. In addition, and as shown in FIG. 7, a vacuum-breaking device may be made by simply placing perforations in the cylinder in such locations as to prevent the user from obtaining a sucking vacuum.

The vacuum-breaking device need not be a cylinder, although a cylindrical shape is preferred. All that the device need to is to break the sucking vacuum when a digit is inserted into the mouth. A cone-shaped device or a closed-end cylinder generally conforming to the shape of the digit and having apertures or air passages to break the sucking vacuum may also be used. Many ways of achieving a vacuum-breaking device are contemplated by this invention and are considered to be equivalent to the invention as claimed.

As shown in FIGS. 1 and 3, it is preferred that the vacuum-breaking device 12 or 14 be firmly secured to the hand so as to prevent aspiration and subsequent choking by the user. Various means of attaching the vacuum-breaking cylinder to the hand of the user are contemplated by this invention. For example, FIG. 1 shows a means for securing a thumb sucking vacuum-breaking device to the hand of the user. It consists of the hollow-cylinder 12 having a first end 30 and a second end 32. The diameter is of sufficient size (FIG. 2) to permit the flow of air from the first end 30 to the second end 32 through passageway 16 formed between the cylinder 12 and the thumb 18. The first end 30 is positioned near the base of the thumb 36 while the second end 32 is located near the tip of the thumb 38. A pad 34 extends from the first end 30 of the cylinder 12 from a portion of the cylinder 12 that faces the index finger 40. Pad 34 generally covers the skin and muscle portion of the hand between the base of the index finger and the base of the thumb. The pad 34 has loops 44 to cooperate with strap 46 so as to allow the strap 46 to engage and cooperate with the pad 34. The loops 34 may be formed by making slits in pad 34.

A wrist pad 50 generally surrounds the wrist 52 of the user except for an open wrist portion that is located below the base of the fifth digit 54. The wrist pad has a plurality of loops 56 that engage and cooperate with band 58 to secure the wrist pad 50 to the wrist.

A means 60 is provided to secure the vacuum-breaking, thumb cylinder 12 to the wrist pad 50. Typically this wrist-pad, vacuum-breaking cylinder, securing means 60 is a strap that extends from the first end 30 of cylinder 12 to the wrist strap in the area of the wrist under the base of the thumb. Strap 60 follows generally the contour of the outer edge of the hand, that is, the edge below the base of the thumb. The fastening means 60 may be an integral part of the vacuum-breaking cylinder 12 and the wrist pad 50 or may be secured appropriately thereto.

As shown in FIGS. 1 and 5, straps 46 and 58 are a part of vertical member 62. Vertical member 62 is generally positioned on the wrist in the open area left by the wrist pad 50, that is, in the wrist area below the base of the fifth digit 54. Straps 46 and 58 are attached to the vertical member 62 or may be formed as an integral part of vertical member 62. As shown in FIG. 5, vertical member 62 has positioned on it two lock posts 64 and 76. Band 46 passes from vertical member 62 diagonally across one side of the hand, through the loops 44 on the webbed pad 34, and then returns diagonally across the opposite side of the hand to vertical member 62. The post 64 on horizontal member 62 is engaged with one on the plurality of holes 70 in the end of band 46. Tab 68 is folded back on vertical member 62 so as to cause locking hole 66 to engage post 64 and lock strap 46 in place. Similarly, band 58 is passed through loops 56 of the wrist pad 50 and passed completely around the wrist to meet vertical member 62. One of the plurality of holes 74 in band 58 is engaged on post 76. Tab 80 is folded back on vertical member 62 so that the locking hole 78 engages the locking post 76 so as to lock band 58 in place. The locking post and hole device (lock button) is made by Precision Dynamics Corporation of San Fernando, Calif.

As shown in FIG. 3, a finger vacuum-breaking device consists of a cylinder 14 placed over a digit 40. A strap 104 extends from the base of the cylinder to a wrist pad 106. Wrist band 110 is threaded through the loops 112 formed by slits 108 in wrist pad 106. The ends of the wrist band 110 are secured to each other with a lock button 114.

An alternate thumb vacuum-breaking device is shown in FIG. 8. An outer band 120 is joined to the base of cylinder 134 and end 122 extends along the thumb side of the hand to the wrist area. A loop 124 extends from near the end 122 of the outer band 120 and receives wrist band through it. Preferably, the loop is made of a semi-rigid (flexible) material so as to allow for easy insertion of wrist band 126.

An inner band 128 has a first tongue 130 and a second tongue 132. First tongue 130 extends from near the base of the cylinder 134 diagonally across one side of the hand to the wrist area below the fifth digit 54 and wraps around the wrist to the other side of the hand. A second tongue 132 extends from near the base of the cylinder 134 diagonally across the other side of the hand to the wrist area below the fifth digit 54 and crosses over first tongue 130. A loop 134 near the end of the first tongue 130 engages one of a plurality of apertures 136 in second tongue 132 where tongues 130 and 132 cross.

After emerging through one of the apertures 136, loop 134 then receives wrist band 126. FIG. 9 shows a cross section of first tongue 130 with loop 134. Tongue 132 crosses over tongue 130 and loop 134 projects therethrough to receive wrist band 126.

After passing through loops 134 and 124, the wrist band 126 is fastened to itself by means of a locking button that consists of a post 142, a lock tab 140, and aperture 144. The post 142 and lock tab 140 are located near one end of wrist band 126. An aperture 144 located at the other end of the wrist band is placed on post 142 after the wrist band surrounds the wrist. The appropriate aperture 144 is selected to provide the appropriate degree of tightness, i.e., at least sufficient to prevent the slippage of the wrist band 126 over the hand. Lock tab 140 is then folded over onto the lock post 142 so as to lock the wrist band 126 in place.

It may be possible that changes in the configurations to other than those shown or described could be used. However, that which is shown or described is typical or preferred. Without departing from the spirit of this invention, it is to be understood that various means for fastening the various components of this invention together may be used or that various parts of the invention can be assembled as a single integral unit.

Therefore it is to be understood that although the present invention has been specifically disclosed with specific examples and preferred embodiments, modifications to the design being the sizing and shape may be apparent to those skilled in the art, and that such modifications and variations are considered to be within the scope of the invention and the appended claims.

I claim:

1. A device for the prevention of thumb and finger sucking comprising a vacuum-breaking device that is placed over at least one digit of a hand and a means for securing said vacuum-breaking device to said hand with a nonreleasable locking mechanism that is unable to be taken apart.

2. The thumb and finger sucking prevention device according to claim 1 with said vacuum-breaking device being cylindrically shaped with a diameter as to permit the flow of air from one end of the device to the other between said digit and the interior wall of said device.

3. The thumb and finger sucking prevention device according to claim 1 with said vacuum-breaking device being of sufficient rigidity so as to prevent the formation of a vacuum seal between said cylinder and said thumb or said finger.

4. The thumb and finger sucking prevention device according to claim 1 with said vacuum-breaking device having an inner surface having longitudinal ridges disposed thereon so as to permit the flow of air in channels between said ridges.

5. The thumb and finger sucking prevention device according to claim 1 wherein said vacuum-breaking device has air-passage perforations therethrough.

6. A finger sucking prevention device according to claim 1 with said device-to-hand securing means comprising:
   a. a separate band surrounding a wrist of said hand;
   b. said locking mechanism securing said wrist band about said wrist; and
   c. means for securing said wrist band to said vacuum-breaking device.

7. A thumb and finger sucking prevention device according to claim 6 with said means for securing said wrist band to said vacuum-breaking device being at least one band extending from said vacuum-breaking device to said wrist band.

8. A finger sucking prevention device worn on at least one finger, a hand and a wrist of a user and comprising:
   a. a hollow, cylindrically-shaped device comprising:
      1) a first end and a second end,
      2) a diameter of sufficient size
         a) to enable said cylindrically-shaped device to fit over said finger so that said first end is near the base of said finger and said second end is near the end of said finger and
         b) to permit the flow of air from said first end to said second end of said cylindrically-shaped device;
   b. a wrist band comprising:
      1) a band having a first end and a second end and of sufficient length to surround said wrist of said user,
      2) a nonreleasable locking means that is unable to be taken apart for fastening said first end and said second end of said band so as to surround said wrist with sufficient tightness so as to render said band incapable of being slipped over said hand of said user and prevent said first end and said second end from being taken apart; and
   c. a means for joining said hollow, cylindrically-shaped device and said wrist band so as to prevent said cylindrically-shaped device from being removed from said finger.

9. The finger sucking prevention device according to claim 9 with said means for joining said cylindrical device to said wrist band comprising a first band extending from said first end of said hollow cylindrical device and from said wrist band and traversing the back of said hand.

10. The finger sucking prevention device according to claim 9 with said means for joining said hollow cylinder to said wrist band comprising a second band extending from said first end of said hollow cylindrical device and from said wrist band and traversing the palm of said hand.

11. A thumb sucking prevention device worn on a thumb, a hand and a wrist of a user and comprising:
   a. a hollow, cylindrically-shaped device comprising:
      1) a first end and a second end,
      2) a diameter of sufficient size
         a) to enable said hollow, cylindrically-shaped device to fit over said thumb so that said first end is near the base of said thumb and said second end is near the end of said thumb, and
         b) to permit the flow of air from said first end to said second end of said cylindrically-shaped device;
   b. a wrist band comprising:
      1) a band having a first end and a second end and of sufficient length to surround said wrist of said user,
      2) a nonreleasable locking means that is unable to be taken apart for fastening said first end and said second end of said band so as to surround said wrist with sufficient tightness so as to render said band incapable of being slipped over said hand of said user and preventing said wrist band from being taken apart; and
   c. a means for joining said hollow, cylindrically-shaped device and said wrist band so as to prevent said hollow, cylindrically-shaped device from being removed from said thumb.

12. The thumb sucking prevention device according to claim 11 with said means for joining said hollow cylindrical device to said wrist band comprising a first band extending from said first end of said hollow cylindrical device at the outer base of said thumb to said wrist band along the edge of the hand generally below the outer base of said thumb.

13. The thumb sucking prevention device according to claim 12 with said means for joining said hollow cylindrically-shaped device to said wrist band comprising a second band comprising a first and second tongue that extend from said first end of said hollow cylindrically-shaped device at the inner base of said thumb to said wrist band in the wrist area generally below the fifth digit with said first tongue of said second band traversing the palm of the hand from said inner base of said thumb to the area of the wrist band below the fifth digit and said second tongue of said second band traversing the back of said hand from said inner base of said thumb to the area of the wrist band generally below the fifth digit of said hand.

14. The thumb sucking prevention device according to claim 13, further comprising:
   a. one or more loops attached near the end of said first tongue, projecting through an aperture of a plurality of apertures near the end of said second tongue in the wrist area below said fifth digit, and then through which the wrist band is passed; and
   b. one or more loops attached near the end of the first band in the wrist area below the thumb and through which the wrist band is passed.

15. A thumb sucking prevention device worn on the thumb, hand and wrist of a user and comprising:
   a. a hollow cylindrical device comprising:
      1) a first and a second end,
      2) a diameter of sufficient size
         a) to enable said hollow cylindrical device to fit over said thumb so that said first end is near the base of said thumb and said second end is near the end of said thumb
      3) a means to permit the flow of air from said first end to said second end of said hollow cylinder;
   b. a web pad extending from said first end of said hollow cylindrical device on the inside of the thumb and conforming in shape generally to the webbed portion of the hand between the thumb and the index finger and having loops therein;
   c. a wrist pad conforming to the shape of the wrist and having loops along the length thereof, said wrist pad leaving an open area in the wrist area below the fifth digit of the hand, and joined to the outside of said first end of said hollow cylindrical device;
   d. a vertical member located in said open area left by said wrist pad below said fifth digit of said hand and having a first and second strap with said first strap traversing one side of the hand, threaded through said loops on said web pad and then traversing the opposite side of said hand and fastened to said vertical member and with said second strap encircling said wrist and threaded through said loops along the length of said wrist pad and fastened to said vertical member.

16. A thumb sucking prevention device worn on a thumb, a hand and a wrist of a user and comprising:
   a. a hollow, cylindrically-shaped device comprising:
      1) a first end and a second end,
      2) a diameter of sufficient size
         a) to enable said hollow, cylindrically-shaped device to fit over said thumb so that said first end is near the base of said thumb and said second end is near the end of said thumb and
         b) to permit the flow of air from said first end to said second end of said cylindrically-shaped device;
   b. a wrist band comprising:
      1) a band having a first and second end and of sufficient length to surround said wrist of said user,
      2) means for fastening said first end and second end of said band so as to surround said wrist with sufficient tightness so as to render said band incapable of being slipped over said hand of said user; and
   c. a means for joining said hollow, cylindrically-shaped device and said wrist band so as to prevent said hollow, cylindrically-shaped device from being removed from said thumb comprising:
      1) a first band extending from said first end of said hollow, cylindrically-shaped device at the outer base of said thumb to said wrist band along the edge of the hand generally below the outer base of said thumb,
      2) a second band comprising a first tongue and a second tongue that extend from said first end of said hollow, cylindrically-shaped device at the inner base of said thumb to said wrist band in the wrist area generally below the fifth digit with
         a) said first tongue of said second band traversing one side of the hand from said inner base of said thumb to the area of the wrist band below the fifth digit and
         b) said second tongue of said second band traversing the other side of said hand from said inner base of said thumb to the area of the wrist band generally below the fifth digit of said hand, and
      3) a loop attached near the end of said first tongue, projecting through an aperture near the end of said second tongue in the wrist area below said fifth digit and receiving said band of said wrist band; and
      4) a loop attached near the end of the first band in the wrist area below the thumb and through which said band of said wrist band is passed.

* * * * *

UNITED STATES PATENT AND TRADEMARK OFFICE
CERTIFICATE OF CORRECTION

PATENT NO. : 5,515,870
DATED : May 14, 1996
INVENTOR(S) : Zilber

It is certified that error appears in the above-indentified patent and that said Letters Patent is hereby corrected as shown below:

Column 6, line 47, after the sentence ending with the numeral "106." the following sentence should be added - - A second band 105 may be similarly placed on the opposite side of the hand. - -

Signed and Sealed this

Eleventh Day of March, 1997

Attest:

Attesting Officer

BRUCE LEHMAN
Commissioner of Patents and Trademarks